(12) United States Patent
Fallon

(10) Patent No.: US 7,138,123 B2
(45) Date of Patent: Nov. 21, 2006

(54) METHODS FOR DIAGNOSING AND TREATING DYSAUTONOMIA AND OTHER DYSAUTONOMIC CONDITIONS

(76) Inventor: Joan M. Fallon, 1234 Central Ave., Suite 1B, Yonkers, NY (US) 10704

( * ) Notice: Subject to any disclaimer, the term of this patent is extended or adjusted under 35 U.S.C. 154(b) by 0 days.

(21) Appl. No.: 10/730,567

(22) Filed: Dec. 8, 2003

(65) Prior Publication Data

US 2004/0115182 A1   Jun. 17, 2004

Related U.S. Application Data

(63) Continuation of application No. 09/929,592, filed on Aug. 14, 2001, now Pat. No. 6,660,831.

(60) Provisional application No. 60/224,991, filed on Aug. 14, 2000.

(51) Int. Cl.
*A61K 39/00* (2006.01)

(52) U.S. Cl. .................. 424/198.1; 514/2; 530/309

(58) Field of Classification Search ................ 530/309; 424/198.1; 514/2
See application file for complete search history.

(56) References Cited

U.S. PATENT DOCUMENTS

| | | | | |
|---|---|---|---|---|
| 5,648,335 A | 7/1997 | Lewis et al. | ................... | 514/12 |
| 5,958,875 A | 9/1999 | Longo et al. | .................. | 514/11 |
| 6,020,310 A * | 2/2000 | Beck et al. | .................... | 514/12 |
| 6,020,314 A | 2/2000 | McMichael | ................... | 514/21 |

FOREIGN PATENT DOCUMENTS

| | | |
|---|---|---|
| EP | 0 564 739 A2 | 10/1993 |
| EP | 0 564 739 A3 | 10/1993 |
| WO | WO 95 22344 A1 | 8/1995 |
| WO | WO 98 22499 A2 | 5/1998 |
| WO | WO 99 64059 A2 | 12/1999 |
| WO | WO 99 64059 A3 | 12/1999 |

OTHER PUBLICATIONS

Barlow, O.W.: A Comparison of the Blood Pressure, Kidney Volume and the Pancreatic Secretory Response Following the Vein Administration of Various Secretin Preparations; American Journ. of Phys. (1927), 81, pp. 182-188.*

Hoshiko et al. The Effect of the Gastrointestinal Hormones on Colonic Mucosal Blood Flow; Acta Medica Nagasakiensia (1994) vol. 39, No. 4, pp. 125-130.*

* cited by examiner

*Primary Examiner*—Patricia Leith
(74) *Attorney, Agent, or Firm*—Maine & Asmus

(57) ABSTRACT

Methods for aiding in the diagnosis of dysautonomic disorders and dysautonomic conditions and methods for treating individuals diagnosed as having a dysautonomic disorder or a dysautonomic condition. In one aspect, a diagnosis method comprising analyzing a stool sample of an individual for the presence of a biological marker wherein the quantity of the biological marker is an indication of whether the individual has, or can develop, a dysautonomic disorder or dysautonomic condition, as well as a therapeutic method for treating a dysautonomic disorder or dysautonomic condition by administration of, e.g., secretin, neuropeptides, peptides and/or digestive enzymes.

1 Claim, 3 Drawing Sheets

FIG. 2

| WEEK | CHYMOTRYPSIN VALUES | |
|---|---|---|
| 0 | | 1$^{ST}$ Infusion |
| 1 | 0.3 | Post 1$^{st}$ Infusion |
| 3 | 1.4 | Post 1$^{st}$ Infusion |
| 6 | 1.2 | Pre 2$^{nd}$ Infusion |
| 7 | 3.6 | Post 2$^{nd}$ Infusion |
| 8 | 3.2 | Post 2$^{nd}$ Infusion |
| 12 | 4.5 | Pre 3$^{rd}$ Infusion |
| 13 | 6.2 | Post 3$^{rd}$ Infusion |
| 16 | 7.5 | Post 3$^{rd}$ Infusion |
| 18 | 7.5 | Pre 4$^{th}$ Infusion |
| 20 | 7.9 | Post 4$^{th}$ Infusion |

FIG. 3

| PATIENT | FC LEVEL | CONDITION |
|---|---|---|
| 1 | 0.5 | Parkinsons |
| 2 | 1.6 | Parkinsons |
| 3 | 0.8 | Parkinsons |
| 4 | 1.2 | Parkinsons |
| 5 | 11.7 | None |
| 6 | 23.9 | None |
| 7 | 13.6 | None |
| 8 | 11.8 | None |
| 9 | 6.6 | Parkinsons |
| 10 | 12 | None |
| 11 | 26.8 | None |
| 12 | 20.2 | None |
| 13 | 19.5 | None |
| 14 | 11.8 | None |
| 15 | 35 | None |
| 16 | 0.6 | Diabetic autonomic failure |
| 17 | 1.2 | Parkinsons |
| 18 | 9.9 | Pakinsons |
| 19 | 12.8 | None |
| 20 | 10.5 | None |
| 21 | 2.4 | Parkinsons |
| 22 | 3.2 | Parkinsons |
| 23 | 26.8 | None |
| 24 | 1.2 | Familial dysautonomia |
| 25 | 3.2 | HSAN II |
| 26 | 6.4 | Orthostatic intolerance |
| 27 | 2.2 | Familial dysautonomia |
| 28 | 3.6 | Parkinsons |
| 29 | 2.2 | Diabetic autonomic failure |

Legend:  FC  Normal > 8.4  Abnormal < 8.4

METHODS FOR DIAGNOSING AND TREATING DYSAUTONOMIA AND OTHER DYSAUTONOMIC CONDITIONS

CROSS REFERENCE TO RELATED APPLICATIONS

This application is a Continuation of U.S. patent application Ser. No. 09/929,592, filed on Aug. 14, 2001 now U.S. Pat. No. 6,660,831, which is based on, and claims the benefit of, U.S. Provisional Application No. 60/224,991, filed on Aug. 14, 2000, which are both fully incorporated herein by reference.

TECHNICAL FIELD OF THE INVENTION

The present invention generally relates to methods for aiding in the diagnosis of dysautonomic disorders and dysautonomic conditions and methods for treating individuals diagnosed as having a dysautonomic disorder or a dysautonomic condition. More particularly, the invention relates to a diagnosis method comprising analyzing a stool sample of an individual for the presence of a biological marker (or marker compound) that provides an indication of whether the individual has, or can develop, a dysautonomic disorder or dysautonomic condition, as well as a therapeutic method for treating a dysautonomic disorder or dysautonomic condition by administration of, e.g., secretin, neuropeptides, peptides and/or digestive enzymes.

BACKGROUND

Familial Dysautonomic (FD), which is also known as Riley Day syndrome, is an autosomal recessive sensory neuropathy that affects approximately 1 in 4,000 individuals of Ashkenazi Jewish descent. This disorder is marked by a reduction of unmyelinated and small myelinated fibers as well as a reduction of doparnine-beta-hydroxylase in the blood. FD decreases both the sympathetic neurons and the peripheral small fibers that modulate temperature regulation. It is thought to arise from both the failure of intrauterine development of neurons and their postnatal development. Symptomology of FD includes, renal disease, corneal ulcerations, mental retardation, loss of pain and vibratory senses, incoordination of movements, diarrhea, esophageal reflux, secretory diarrhea, gastrointestinal paresis, hypotension, facial abnormalities, altered dentition, increased salivary secretion, abnormalities of the sweat glands, bowel distension, fecal impaction, prolonged QT intervals (>440), risk of sudden death, and orthostatic syncope. Further features include decreased pain sensation, decreased temperature regulation, difficulty feeding, lack of overflow tears while crying, recurrent pneumonias, scoliosis or hyperkinesis, increased sweating and skin blotching, decreased stature, as well as other conditions associated with autonomic dysfunction.

Currently the underlying biochemical and genetic defects which cause the FD disorder are unknown. The gene which causes this disorder has been mapped to chromosome 9, in the q31-33 region. Presently, there is no prenatal screening test for this condition, and there is no early detection of the condition other than the presence of symptomology.

There are a plethora of is dysautonomic disorders and/or disorders in which symptomologies of autonomic dysfunction are manifest. For instance, Parkinson's disease is marked by mild to severe autonomic dysfunction, including changes in gait, tremor, discoordination, increased salivary flow, and overall loss of autonomic function. Additionall, changes in executive function are typically noted in a Parkinson's patient, often times allowing the patient to appear as having Alzheimer's disease and resulting in misdiagnosis. Executive function disorders are also found in autistic children.

It is known that Parkinson's disease is caused by a deficient state of levo-dopamine in the brain. More specifically, levo-dopa induced dyskinesis in Parkinson's patients is thought to be a result of deprivation of the substantia nigra. To this date, medical science has not found a substrate that would allow an injectable form of l-dopa to reach the brain and successfully cross the blood brain barrier. The current dopamine replacement therapy is aimed at either direct replacement or mimicking the action at the dopamine receptor sites in the brain. Sinemet™ and Sinemet CR™ are the two major drugs suited to that end. While the levodopa-therapy can create some beneficial changes initially, those changes generally wane over time, and produce other problems such as severe sleep disturbance, dyskinesis, and constant nausea. Medical approaches to Parkinson's disease include surgical destruction of the tissue of the brain and the insertion of microelectrodes (deep brain electrical stimulation) to effected portions of the brain. The insertion of electrodes has the advantage of being reversible. These interventions, however, are generally transient and neither produce a permanent change in the Parkinsonian state nor reverse the effects of the disease.

Parkinson's disease is widespread throughout the Western hemisphere and was first reported by physician James Parkinson in 1817. Parkinson's disease is first detected as a tremor in a limb, and ultimately progresses to include 3 manifestations: (i) rigidity, which is characterized by "cogwheel" like movement and "lead-pipe" rigidity; (ii) bradykinesia or slowness in movement, and (iii) postural instability associated with a stooped stance and an impaired gait. These altered movements are features of the motor dysfunction, but in addition there can be a mental impairment in as many as 40% of all Parkinson's patients.

Some authors suggest that Parkinson's disease is a multifactor neurodegenerative disorder, which evolves due to excessive oxidation. The substantia nigra is susceptible to oxidative damage, which supports this theory of the formation of Parkinson's disease. Abnormalities of the oxidative phosphorylation impair the mitochondria of the substantia nigra, and intensify free radical generation.

While the dyskinesis and loss of executive functioning of the brain receive the most significant mention with respect to Parkinson's, other manifestations exist that are associated with autonomic dysfunction, which are often poorly understood. Some of these manifestations include, e.g., esophageal reflux, diarrhea, and other gastrointestinal dysfunction. In addition, excessive sweating, sleep disturbances and still other symptoms of Parkinson's disease are very similar to those found in Familial Dysautonomia.

Guallaine-Barre Syndrome (GBS) is characterized as an acute autoimmune polyradiculopathy. It generally manifests as a flaccid paresis coupled with areflexia, sensory loss and disturbance, as well as an elevated cerebrospinal fluid protein level. There are multiple variations of GBS, each of which displays a specific subgrouping of symptoms, including those of the Miller Fisher Syndrome group. GBS seen primarily in the United States constitutes a subtype best characterized as a demyelinating type. In the past, GBS was thought to be caused by numerous factors such as the presence of an antecedent viral infection. The most recent hypothesis points to the presence of an antecedent infection of *Campylobacter jejuni* gastroenteritis. It is further postulated that the presence of this infection produces inflammation of the brain and nervous system and gastrointestinal tract.

Further, a correlation between ketoacidosis and GBS was recently discovered, whereby a patient with diarrhea and fever in a comatose state had a serum blood glucose level of 672 mg/dl, with the presence of urinary ketone bodies. This pancreatic role in the potential formation of GBS (as well as other dysautonomic conditions) is of note and is addressed by the present invention.

Furthermore, tumors of differing types can also produce dysautonomic symptomology. For example, pheochromocytoma is a well-encapsulated, lobular, vascular tumor, which can occur anywhere in the body. It is made up of chromaffin tissue of the adrenal medulla, or sympathetic paraganglia. Hypertension is the most apparent symptom, reflecting the increased secretion of epinephrine and norepinephrine, and may be either persistent or intermittent. Attacks may occur anywhere from every few months to several times daily, and typically last less than five minutes. Physical and emotional stresses can initiate an attack. During severe attacks, patients may experience headache, sweating, apprehension, palpation, tremor, pallor or flushing of the face, nausea and vomiting, pain in the chest and abdomen, and paresthesias of the extremities, weight loss, and orthostatic hypotension. Inflammation is a hallmark of this condition. Interestingly, these symptoms are common to many other dysautonomic conditions. Chemodectoma is another type of tumor, characterized as any benign, chromaffin-negative tumor of the chemoreceptor system. The most common types of chemodectoma are the carotid (the principal artery in the neck) body tumor and the glomus jugulare tumor, and it is also known as nonchromaffin paraganglioma.

Neuroblastoma, a type of sarcoma, consists of malignant neuroblasts, which typically arise in the autonomic nervous system, or in the adrenal medulla. It is considered a type of neuroepithelial tumor and affects mostly infants and children up to the age of ten. Eighty five percent of cases occur prior to age six, and arise from immature undifferentiated neuroblasts of neural crest origin. Two-thirds of neuroblastomas occur in an adrenal gland, but may also appear where sympathetic nerves are present, such as in the chest, pelvis, abdomen, and neck. Symptoms may include fever, weight loss, weakness, abdominal discomfort, anorexia, anemia, bone pain, proptosis, pallor, periorbital ecchymoses, easy bruising, neurological manifestations, and metastic subcutaneous nodules, and possible hypertension.

Next, Dopamine-b-Hydroxalase Deficiency is characterized by both sympathetic noradrenergic deprivation and adrenomedullary failure, and intact vagal and sympathetic cholinergic function. It is a rare, congenital, non-hereditary form of severe orthostatic hypotension, caused by complete absence of Dopamine-b-Hydroxylase, the enzyme involved in the conversion of dopamine to norepinephrine. The presence of orthostatic hypotension has not been documented in those who are afflicted with Db H deficiency prior to the age of 20. However, during childhood, impaired exercise tolerance, fatigue, and episodes of fainting and syncope, are frequently present. Symptoms from orthostatic intolerance worsen in late adolescence and in early adulthood. Patients experience more intense symptoms due to orthostatic intolerance in the morning hours, heat, and after alcohol consumption, though they do not experience symptoms after eating. Upon physical examination, patients may reveal a low normal (supine) blood pressure and a low (supine) heart rate. In the upright position, systolic blood pressure always falls below 80 mm Hg. However, opposite of other forms of autonomic failure, the compensatory rise in heart rate is completely preserved. Sweating is normal, and the pupils may be somewhat small, but respond to light and accommodations.

Baroreflex failure may present itself by essential hypertension, uncontrolled severe hypertension, pheochromocytoma, or, less commonly, damage to the glossopharyngeal or vagal nerves. Patients with baroreflex failure may have severe hypertension, either sustained or episodic. Blood pressures can reach 170–280/110–135. Accompanying tachycardia may suggest the diagnosis of pheochromocytoma, which is supported by sensations of warmth and or flushing, palpitations, headache, and diaphoresis.

Aromatic L-Amino Acid Decarboxylase Deficiency is a disorder caused by a deficiency of an enzyme of the lyase class that catalyzes the decarboxylation of aromatic amino acids, notably converting dopa to dopamine, tryptophan to triptamine, and hydroxytryptophan to serotonin. The enzyme is then bound to a pyridoxal phosphate cofactor and occurs particularly in the liver, kidney, brain and vas deferens. Symptoms of the disease may include temperature instability, ptosis of the eyelids, hypersalivation, distal chorea, swallowing difficulties, drowsiness, irritability, truncal hypotonia, oculogyric crises, and pinpoint pupils.

Tetrahydrobiopterin Deficiency is a disorder whereby a defect in enzymes required for the synthesis of catecholomines results in a deficiency of neurotransmitters. Symptoms begin between two and eight months of age, and include unstable body temperature, swallowing difficulties, hypersalivation, pinpoint pupils, ptosis of the eyelids, decreased mobility, drowsiness, and irritability.

Familial Paraganglioma Syndrome is another tumor related disease. Due to the chemoreceptor function of the carotid body, these tumors were first called chemodectomas or carotid body tumors, though carotid body paraganglioma is the most accurate terminology for these lesions. Paraganglioma tumors that develop from the paraganglia adjacent to the vagus nerve and the jugular bulb are usually described as glomus vagale and glomus jugulare. Paraganglioma tumors are quite rare and account for less than 1000 reported cases since 1980.

As for clinical presentation, cervical paragangliomas include dysphonia, aspiration, hearing loss, dysphagia, tinnitus, pain, chronic cough, and shoulder weakness (due to tumor encroachment on cranial nerves).

In 1960, two researchers, Dr. Milton Shy at the National Institutes of Health, and Dr. Glen Drager at Baylor College of Medicine in Houston, Tex., described a common set of neurological manifestations associated with autonomic failure. Originally called the "Shy-Drager Syndrome," this complex syndrome is currently referred to as "Multiple System Atrophy" or MSA. The American Autonomic Society has defined MSA in the following manner: "MSA is a sporadic, progressive, adult onset disorder characterized by autonomic dysfunction, Parkinsonism, and ataxia (a failure of muscular coordination) in any combination. The features of the disorder include Parkinsonism Cerebellar or Corticospinal Signs, Orthostatic Hypotension, Impotence, Urinary Incontinence or Retention, usually preceding or within two years after the onset of the motor symptoms. Parkinson and cerebellar features commonly occur in combination. However, certain features may predominate. It is important to note that these manifestations may occur in various combinations and may also evolve over time.

Next, it is estimated that over 500,000 Americans are afflicted with Orthostatic Intolerance. Despite the enormity of the number, these conditions are among the least understood of the autonomic disorders. Orthostatic Intolerance predominately affects younger individuals, particularly females, and often those under the age of thirty-five. The onset can be sudden, and the impact can be significant on both lifestyle and on the capacity to work. Often, these conditions tend to be misdiagnosed as either a psychiatric or anxiety-related disorders, due to the nature of the symptoms.

Standing upright results in a series of reflexive bodily responses, regulated by the Autonomic Nervous System, to compensate for the effect of gravity upon the distribution of blood. Orthostatic Intolerance results from an inappropriate response to this change in body position. The normal response for a change in body position is stabilization to the upright position in approximately sixty seconds. During this process, the normal change in heart rate would include an increase in heart rate of 10 to 15 beats per minute, and an increase in diastolic pressure of 10 mm Hg, with only a slight change in systolic pressure. For those who are afflicted with Orthostatic Intolerance, there is an excessive increase in heart rate upon standing, resulting in the cardiovascular system working harder to maintain blood pressure and blood flow to the brain.

The upright posture also brings about a neurohumoral response, involving a change in the levels of vasopressin, renin, angiotensin and aldosterone levels—all of which are involved in the regulation of blood pressure. Additionally, arterial baroreceptors, particularly those in the carotid sinus area, play an important role in the regulation of blood pressure and the response to positional changes. As the heart pumps blood to the body, the left atrium is passively filled with blood as a result of the force exerted by venous blood pressure. The baroreceptors in the left atrium respond proportionately to the pressure exerted by venous blood pressure. Thus, a drop in venous blood pressure will trigger a compensatory response to increase blood pressure. Any disruption in any of these processes, or their coordination, can result in an inappropriate response to an upright position and a series of symptoms, possibly including syncope.

Neurally Mediated Syncope, also known as Neurocardiogenic Syncope, is another disorder characterized by autonomic dysfunction. More specifically, neurocardiogenic syncope is a complex and common disturbance of the autonomic nervous system that can lead to sudden drops in blood pressure leading to fainting. The medical term for fainting is syncope, coming from the Greek term "syncopa", meaning "to cut short." Syncope has many causes, and therefore discerning the exact cause can be difficult. Over the last several years, much has been learned about one particular cause of fainting—the disorder now known as neurocardiogenic syncope. Neurocardiogenic syncope is also known as vasovagal syncope or neurally mediated syncope. It describes a transient failure of the brain to adequately regulate the body's blood pressure and heart rate. The exact cause(s) are still unclear, but a basic understanding is evolving. The blood pressure control centers are located in the posterior parts of the brain (the brainstem or medulla). Every time a person stands, gravity pulls blood toward the lower extremities. The brain senses this change and compensates by increasing the heart rate and tightening (constricting) the blood vessels of the legs, forcing blood back upward to the brain. These centers in the brainstem (the autonomic centers), then work as a sort of thermostat to regulate blood pressure. In neurocardiogenic syncope, the system periodically breaks down, allowing the blood pressure to fall too low, and causing the brain to lose its blood supply resulting in loss of consciousness (fainting). These episodes frequently begin in adolescence following periods of rapid growth, although they can occur at any age.

Tilt table testing is used to determine a person's susceptibility to these episodes. This test involves the strapping of a patient to a special table, slowly inclining upward to an angle of between 60 and 80 degrees, and kept up for around thirty minutes. This provides a constant low stress (gravity) that should be easily tolerated by a person with normal autonomic function. However, for patients with poor autonomic control, this relatively mild stress will provoke a sudden fall in heart rate and blood pressure. Some centers will also use a synthetic form of adrenaline (isoproterenol) as an additional stress.

Therapy for patients with neurocardiogenic syncope has to be individualized to fit that person's specific needs. Many patients with neurocardiogenic syncope need only avoid predisposing factors (such as extreme heat or dehydration), though some will require medical therapy to prevent further fainting spells. A variety of different medications are used, and no one therapy works for everyone. Some patients may require therapy with low doses of two or three agents in combination, which is often tolerated better than a very high dose of a single agent.

Sudden Infant Death Syndrome (SIDS), also known as fetal fatal insomnia, is considered to be of unknown etiology and usually occurs during sleep. The postmortem examination of children who have died as a result typically does not reveal the cause of death, hence the label sudden infant death syndrome (SIDS). Recent research has pointed in many directions with respect to SIDS.

One theory for the cause of SIDS points again to the role of reflux. Once thought to be a normal postmortem finding, the evidence of gastro esophageal reflux postmortem indicates this as a possible contributory factor. Other theories point to the role of nerve damage or nerve malfunction as playing a contributory role in the formation of SIDS. One study demonstrates a marked prolonged QT interval in those who are at risk for SIDS. Researchers have documented that a child having a SIDS "attack" who was brought to the hospital was suffering from a prolonged QT interval. Even though the child survived the episode, it revealed an interesting piece of information.

The role of hypothalamic failure has also been postulated as a cause of SIDS. This failure precludes the infant from sensing temperature changes in the body, much like that of the child with dysautonomia. It is therefore postulated in accordance with the present invention that autonomic dysfunction plays a role, either primary or secondary, in the incidence of SIDS.

Interestingly, the dysautonomic conditions described above have a gastrointestinal component. Indeed, as with Guillaine-Barre wherein it is postulated that a GI pathogen is a causative factor in the formation of the dysautonomia, it is possible that other dysautonomic conditions have GI components.

It was recently discovered that the administration of secretin, a gastrointestinal peptide hormone, to children diagnosed with autism resulted in ameliorating the symptoms associated with autism. This finding was published in the article by Horvath et al., entitled *Improved Social and Language Skills After Secretin Administration In Patients with Autistic Spectrum Disorders*, Journal of the Association for Academic Minority Physician Vol.9 No.1, pp. 9–15, January, 1998. The secretin administration, as described in Horvath, was performed as a diagnostic procedure, i.e., to stimulate pancreaticaobiliary secretion during an upper gastrointestinal endoscopy, rather than as a therapeutic procedure. Although the specific mechanism by which the secretin improved the autistic-related symptoms was not specifically identified, Horvath postulated that secretin may have had a direct or indirect effect on the central nervous system. What is important, however, is that this was the first time that gastrointestinal problems of autistic children were linked to a possible etiology in autism.

It has been found by the present inventor that populations of autistic children suffer from GI disturbances and other conditions which are dysautonomic in nature. Thus, in general, these findings are believed by the present inventor to be a possible link between the etiology of autism and autonomic dysfunction.

Accordingly, in view of such findings, a method for determining whether an individual suffering from a dysautonomic disorder and/or any disorder comprising dysautonomic components will benefit from the administration of secretin, other neuropeptides, peptides and/or digestive enzymes, would be highly advantageous. In addition, a method for aiding in the diagnosis of individuals who may develop dysautonomic disorders conditions and symptoms is highly desirable.

SUMMARY OF THE INVENTION

The present invention is directed to methods for aiding in the diagnosis of dysautonomic disorders and dysautonomic conditions, and for treating individuals diagnosed as having dysautonomic disorders or dysautonomic conditions including, but not limited to, Familial Dysautonomia (FD) (or Riley-Day Syndrome), Guillaine-Barre Syndrome (GBS) (or acute idiopathic polyneuropathy), Parkinson's disease, fetal fatal insomnia (FFI), diabetic cardiovascular neuropathy, Heredity Sensory and Autonomic Neuropathy type III (HSAN III), central autonomic disorders including multiple system atrophy (Shy-Drager syndrome), orthostatic intolerance syndrome including mitral valve prolapse, postural tachycardia syndrome (POTS), and idiopathic hypovolemia, dysautonomic syndromes and disorders of the catecholamine family including baroreflex failure, dopamine-B-Hydroxylase deficiency, pheochromocytoma, chemodectina, familial paraganglioma syndrome, tetrahydrobiopterin deficiency, aromatic-L-amino acid decarboxylase deficiency, Menke's disease, monoamine oxidase deficiency states, and other disorders of dopamine metabolism, dysautonomic syndromes and disorders of the cardiovascular system, Chaga's disease, Diabetic autonomic failure, pure autonomic failure, syncope, hypertension, cardiovascular disease, renal disease and SIDS.

In one aspect, methods are provided for treating all types of dysautonomia and disorders with autonomic components by the admininsration of secretin, CCK(Choleystichenin), VIP (Vasoactive Intesinal Peptide), other neuropepetides and peptides, and/or digestive enzymes.

In another aspect, diagnostic methods are provided for determining whether an indivudual has, or can develop, a dysautonomic disorder or condition, and for determining whether an individual will benefit from the administration of secretin, CCK, VIP, other neurpeptides and peptides, and/or digestive enzymes for treating a dysautonomic disorder or condition. A preferred diagnostic method comprises analyzing a compound in a stool sample of an individual, and correlating the analysis of the compound with a dysautonomic disorder or condition or lack thereof. In one embodiment, the stool compound comprises a pancreatic enzyme such as chymotrypsin, or any compound that provides an indication of either protien digestion or metabolism, pancreatic function, or an inflammatory process, or a combination thereof. Preferably, the step of analyzing comprises determining a quantitative level of the compound in the stool.

In another aspect, a method for treating a dysautonomic disorder with secretin comprises the step of administering to an individual having the disorder an effective amount of secretin to improve a symptom of the disorder.

In yet another aspect, a method for treating a dysautonomic disorder with secretin comprises the steps of analyzing a compound in a stool sample of the individual, wherein the administration of secretin is based on the analysis of the stool sample.

In another aspect, the stool compound comprises a pancreatic enzyme such as chymotrypsin, or any compound that provides an indication of either protein digestion or metabolism, pancreatic function, or an inflammatory process, or a combination thereof.

In yet another aspect, a process of analyzing the stool sample comprises the steps of measuring a quantitative level of a pancreatic enzyme (such as chymotrypsin) present in the stool sample, and comparing the measured quantitative level with at least one threshold level to determine the efficacy of secretin administration to the individual. In one embodiment, the threshold level is based on a level of the pancreatic enzyme associated with at least one other individual of the same approximate age that does not have the dysautonomic disorder.

These and other aspects, features, and advantages of the present invention will be described and become apparent from the following detailed description of preferred embodiments, which is to be read with the accompanying drawings.

BRIEF DESCRIPTION OF THE DRAWINGS

FIG. 2 is a table diagram illustrating measured chymotrypsin levels of an individual subjected to secretin infusions to treat a dysautonomic condition; and FIG. 3 is a table diagram illustrating measured chymotrypsin levels of a plurality of individuals, some of which have a dysautonomic condition.

DETAILED DESCRIPTION OF PREFERRED EMBODIMENTS

Figure 1:
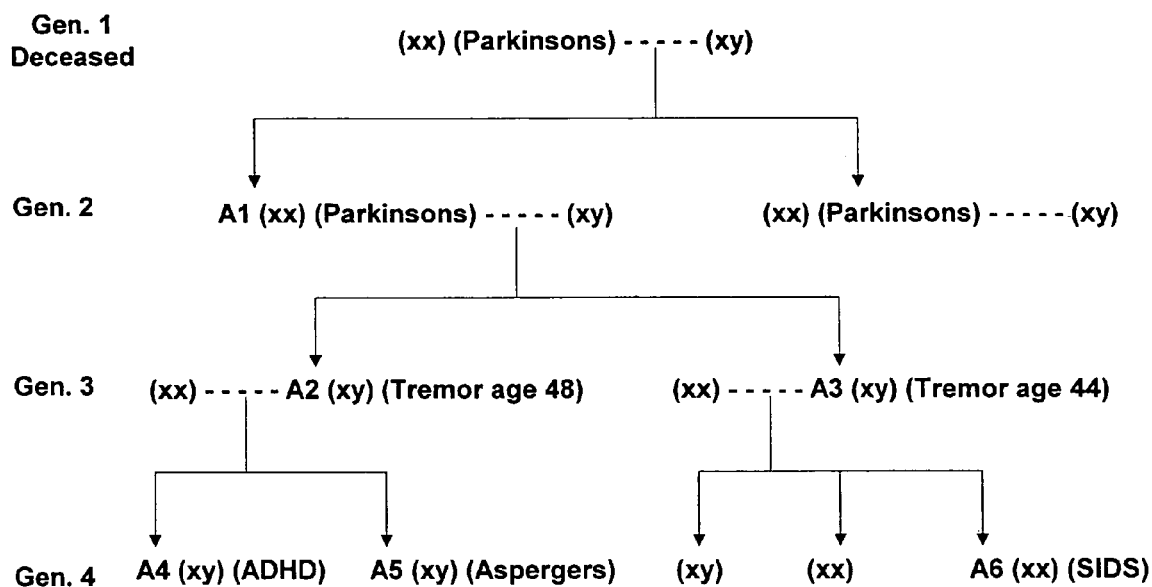
FIG. 1 is a diagram of a family tree illustrating a correlation between dysautonomic conditions and other disorders.

The present invention is directed to methods for aiding in the diagnosis of dysautonomic disorders and dysautonomic conditions, and for treating individuals diagnosed as having a dysautonomic disorder such as Familial Dysautonomia and other disorders having dysautonomic components. In a preferred embodiment, a method is provided for determining the presence of abnormal protein digestion and/or pancreatic dysfunction of an individual, especially a child, by analyzing a stool sample of the individual for the quantitative levels of one or more pancreatic enzymes, including, but not limited to, chymotrypsin, so as to determine if the individual has, or can develop, a dysautonomic disorder or condition. Further, a method is provided for determining whether the individual is likely to benefit from the administration of secretin, CCK, VIP, digestive enzymes, and/or other peptides and/or neuropeptides. Until now, there has been no clear biological marker for dysautonomic disorders or conditions to allow early diagnosis or screening of such disorders or conditions.

As noted above, it was recently discovered that the administration of secretin, a gastrointestinal peptide hormone, to children diagnosed with autism resulted in ameliorating the symptoms associated with autism. Subsequently, the inventor herein discovered that a sub-population of autistic children had, abnormal to pathologic levels of a pancreatic enzyme such as chymotrypsin in their stools. The inventor herein further discovered that the sub-population of autistic children who bad low levels of fecal chymotrypsin were positive responders to a therapeutic method for treating autism comprising administration of, secretin and/or digestive enzymes. It was further discovered that a sub-population of individuals suffering from ADD (attention deficit disorder) and/or ADHD (attention deficit hyperactivity disorder) who had low levels of fecal chymotrypsin were positive responders to a therapeutic method comprising administration of; secretin and/or digestive enzymes. These findings are described in detail in U.S. patent application Ser. No. 09/466,559, filed Dec. 17, 1999, entitled "Methods For Treating Pervasive Development Disorders," and U.S. patent application Ser. No. 09/707,395, filed on Nov. 7, 2000, entitled "Methods For Treating Pervasive Development Disorders", both of which are commonly owned and incorporated herein by reference.

It has also been discovered by the present inventor that populations of autistic children suffer from GI disturbances and other conditions which are dysautonomic in nature. Moreover, as explained below, and in accordance with the present invention, it has been discovered by the inventor herein that a population of individuals suffering from dysautonomic disorders such as FD and Parkinson's have abnormal or pathologic levels of pancreatic enzymes such as chymotrypsin in their stools. Thus, these findings are believed to indicate a possible link between the etiology of autism, ADD, ADHD and autonomic dysfunction. For example, it is postulated that in dysautonomic syndromes, the partial paresis of the gastrointestinal tract, and therefore the lack of functioning of the secretory cells of the proximal small intestine, preclude the proper formation and or release of secretin. It is further postulated that this abnormal protein digestion as reflected by the low levels of pancreatic enzymes such as chymotrypsin, can be improved by the administration of secretin, CCK, VIP, other neuropeptides, peptides and/or digestive enzymes to thereby ameliorate the symptomologies of dysautonomic conditions. Indeed, as low measures of fecal chymotrypsin, for example, expresses an abnormality of protein digestion and/or pancreatic dysfunction, it is postulated tat an improvement of protein digestion to promote nonnal growth and development of an individual suffering from a dysautonomic disorder or dysautonomic condition by the administration of secretin, CCK, VIP, other neuropeptides and/or peptides and/or digestive enzymes, can ameliorate the dysautonomic symptomatologies.

The following case studies support the above findings. Further, preferred methods for diagnosing and treating dysautonomic disorders and dysautonomic conditions in accordance with the invention are described. It is to be understood that these examples are set forth by way of illustration only, and nothing therein shall be taken as a limitation upon the overall scope of the invention.

Case 1

FIG. 1 is a diagram of a family tree over four generations of a family known for having Parkinson's, SIDS and ADD/ADHD and learning disabilities. As shown, each of the generations 1 through 4 demonstrate a related condition. In generation 1, one parent had Parkinson's disease. In generation 2, A1 has Parkinson's disease. In generation 3, A2 and A3 suffered from tremors for 2 and 1 years, respectively. In generation 4, A4 has ADHD and is learning disabled, A5 suffers from Aspergers (a form of PDD) and A6 suffered from SIDS. The family tree demonstrates a connection between dysautonomia, SIDS and ADD/ADHD. It is postulated that if Parkinson's, SIDS and FFI could result from a prolonged QT interval, and that these dysautonomic conditions could be linked together, the fecal chymotrypsin levels, for example, would be abnormal.

Certain members of the family in FIG. 1.(i.e., A1, A2, A4 and A5) were examined by analyzing their fecal chymotrypsin. In a preferred embodiment, a fecal chymotrypsin test comprises the following steps. First, approximately 2 grams of stool is collected from an individual and placed in a sterile container (although it is to be understood that any quantity of stool may be collected, as 2 grams of stool is not a required amount). The stool sample is analyzed using, e.g., an enzymatic photospectrometry analysis as is known by those skilled in the art, to determine the level of fecal chymotrypsin in the stool. Although the enzymatic photospectrophotometry process is preferred, any suitable conventional method may be used for measuring fecal chymotrypsin.

After determining the chymotrypsin level in a stool sample, the chymotrypsin level is compared with a normal threshold chymotrypsin level. By way of example, with the fecal chymotrypsin tests of the stool samples being performed at 30 degrees C., normal levels of chymotrypsin are deemed to lie above 8.4 U/gram, whereas pathologically abnormal levels are deemed to lie below 4.2 U/gram. In addition, a chymotrypsin level between 8.4 U/gram and 4.2 U/gram is considered equivocal, and further testing of the individual's fecal chymotrypsin levels over a period of time should be performed. In another embodiment, the threshold chymotrypsin level is based on a level of chymotrypsin associated with at least one other individual of the same approximate age that does not have the dysautonomic disorder.

Using the above fecal chymotrypsin test, the results were as follows. A1, A2, A4 and A5 each demonstrated abnormal fecal chymotrypsin levels, 0.1 U/gm, 1.6 U/gm, 2.2 U/gm and 1.8 U/gm, respectively. The fecal chymotrypsin of A3 and A6 were not tested.

Case 2

A 6 year old male child previously diagnosed with Familial Dysautonomia presents with marked autonomic dysfunction, including a total inability to walk or talk. The child lacked fine motor movements, and underwent an autonomic crisis 5–7 times per day, which necessitated continuous skilled nursing with life support equipment including a respirator in close proximity. The child was fed with a food pump, and had to have his bowel evacuated by hand due to the near total anesthesization of the small and large intestines. Fundal Plication was performed in order to deduce the incidence of influx, and excessive drooling was continually present. The child was completely dependent upon his care givers, and was classified during his first year of life as having autistic qualities.

The child was administered ongoing secretin infusions. A preferred secretin infusion process includes the initial step of prepping an and of the individual with an IV injection of saline. A test dose of 1 U of, e.g., Secretin-Ferring is then administered to the individual. Approximately one minute after infusion, the individual is examined for signs of allergic reaction including rash, increased heart rate, and increase of blood pressure. If the individual does not display any signs of allergic reaction, the remaining units of Secretin-Ferring is administered to the individual in the manner of an IV push, which is then followed by a saline flush. Subsequently, the individual receives a 1–2 U/kg of body weight infusion of Secretin-Ferring via an IV push method approximately every 4 weeks for 8 months.

It is to be understood that any commercially available form of secretin may be used. Furthermore, treatment of a dysautonomic condition can be made by the administration of an effective amount of secretin, neuropeptide, CCK, VIP, peptides and or digestive enzymes through one of intravenous, transderntaal, intranasal, small molecule or a combination thereof, or other suitable methods of administration.

After the 4th secretin administration, the child began to exhibit significant changes in his behavior as well as significant changes in his autonomic dysfunction. The child began to walk and utter words. His loss of blood pressure and autonomic crises became non-existent, his need for a nurse practitioner was completely eliminated, and he was able to work with an aide who helped him ambulate.

Case 3

A child diagnosed as having FD was administered a fecal chymotrypsin test using the test described above on a stool sample obtained from the child comprising about 2 grams of stool. As shown in FIG. 2, the initial fecal chymotrypsin level of the child was determined to be 0.3 U/gram, which falls significantly below the preferred normal threshold of 8.4 U/gram. The child was administered a 1–2 U/kg of body weight infusions of Secretin-Ferring via an IV push method over a 20 week period and stool samples were analyzed either pre or post infusion. The results shown in FIG. 2 demonstrate that the child's fecal chymotrypsin level progressively increased with the secretin infusions.

Case 4

The fecal chymotrypsin of 10 adults with previously diagnosed Parkinson's Disease were analyzed using the test described above. Further, 4 adults and 2 children with other dysautonomic conditions including diabetic autonomic failure, orthostatic intolerance syndrome, Familial dysautonomia and HSAN III were administered a fecal chymotrypsin test, and 13 adults the same age with no known condition were administered a fecal chymotrypsin test.

As shown in FIG. 3, 9 out of 10 Parkinson's patients had abnormal fecal chymotrypsin levels. Each of the age matched adults did not exhibit an abnormal fecal chymotrypsin level. All 4 patients with other dysautonomic conditions exhibited an abnormal fecal chymotrypsin level (e.g., below 8.4 U/gm). All 13 normal subjects had fecal chymotrypsin levels within the normal range.

Case 5

4 children were administered secretin in the amount of 1 U/kg. Table 1 below demonstrates the changes observed where "BP" denotes is blood pressure and FC denotes fecal chymotrypsin level. As shown in Table 1, a significant decrease in blood pressure was observed in each child immediately after the administration of secretin. Additionally, a flush similar to that of niacin sensitivity was observed in 3 children.

TABLE 1

| Child | AGE | FC | BP prior | 1 min | 5 min | 10 min | observations |
|---|---|---|---|---|---|---|---|
| 1 | 4 | 1.7 | 120/70 | 90/60 | 95/65 | 100/65 | Facial flush |
| 2 | 2 | 3.3 | 110/80 | 80/50 | 90/60 | 90/60 | Whole body flush |
| 3 | 6 | 2.0 | 130/85 | 100/70 | 100/70 | 105/85 | Sweating |
| 4 | 6 | 2.6 | 120/60 | 90/50 | 95/50 | 100/70 | Facial flush |

Case 6

2 adults were administered secretin in the amount of 1 U/kg. Table 2 below demonstrates the changes reported. Adult #2 reported having some hypertension prior to the administration of secretin. She reported having no difficulty with her hypertension for 6 months post administration.

TABLE 2

| Adult | AGE | BP Prior | 1 Min | 10 Min | Description |
|---|---|---|---|---|---|
| 1 | 33 | 110/70 | 90/70 | 100/65 | Facial Flush |
| 2 | 29 | 135/85 | 100/70 | 100/70 | Facial flush |

In summary, the results of the case studies described herein demonstrate that dysautonomic disorders may be treated with the administration of secretin, CCk, VIP, and other neuropeprides and peptides and/or digestive enzymes. Furthermore, the results indicate that the quantitative level or activity of pancreatic enzymes in a stool sample, such as fecal chymotrypsin, can be used to determine if an individual has, or can develop, one or more dysautonomic disorders or conditions. Further, pancreatic enzymes such as chymotrypsin can be used as biological markers to determine the efficacy of administering secretin, CCk, VIP, and other neuropeptides and peptides and/or digestive enzymes to an individual having a dysautonomic disorder or condition to thereby treat the individual. Indeed, the above case studies indicate that the administration of secretin, CCK, VIP, and other neuropeptides and peptides and/or digestive enzymes to such individuals having, for example, subnormal to pathologic levels of fecal chymotrypsin, will result in the amelioration of symptomologies of such disorders.

Although illustrative embodiments have been described herein with reference to the accompanying drawings, it is to be understood that the present invention is not limited to those precise embodiments, and that various other changes and modifications may be affected therein by one skilled in the art without departing from the scope or spirit of the invention. All such changes and modifications are intended to be included within the scope of the invention as defined by the appended claims.

What is claimed is:

1. A method of treating hypertension in a human, the method comprising the step of administering a composition consisting of secretin in an amount of at least 1 U/kg of body weight of the human.

* * * * *